United States Patent
Lummis et al.

(10) Patent No.: US 8,568,394 B2
(45) Date of Patent: Oct. 29, 2013

(54) OPHTHALMIC INTERFACE APPARATUS AND SYSTEM AND METHOD OF INTERFACING A SURGICAL LASER WITH AN EYE

(71) Applicant: AMO Development, LLC., Santa Ana, CA (US)

(72) Inventors: Wesley Lummis, Oceanside, CA (US); Ronald M. Kurtz, Irvine, CA (US)

(73) Assignee: AMO Development LLC, Santa Ana, CA (US)

( * ) Notice: Subject to any disclaimer, the term of this patent is extended or adjusted under 35 U.S.C. 154(b) by 0 days.

(21) Appl. No.: 13/649,849

(22) Filed: Oct. 11, 2012

(65) Prior Publication Data
US 2013/0035674 A1    Feb. 7, 2013

Related U.S. Application Data

(60) Division of application No. 11/948,433, filed on Nov. 30, 2007, now abandoned, which is a continuation-in-part of application No. 11/277,477, filed on Mar. 24, 2006, now Pat. No. 7,371,230, which is a continuation of application No. 10/865,165, filed on Jun. 10, 2004, now Pat. No. 7,018,376, which is a division of application No. 09/772,539, filed on Jan. 29, 2001, now Pat. No. 6,863,667.

(51) Int. Cl.
*A61F 9/009*    (2006.01)

(52) U.S. Cl.
USPC ............ 606/5; 606/4; 606/6; 606/10; 606/13; 606/166

(58) Field of Classification Search
USPC ............................................................ 606/5
See application file for complete search history.

(56) References Cited

U.S. PATENT DOCUMENTS

| 4,932,968 A | 6/1990 | Caldwell et al. |
| 5,009,660 A | 4/1991 | Clapham |

(Continued)

FOREIGN PATENT DOCUMENTS

| EP | 766540 A1 | 4/1997 |
| WO | WO9615712 A1 | 5/1996 |

(Continued)

OTHER PUBLICATIONS

Ito M., et al., "Picosecond Laser in Situ Keratomileusis with a 1053-nm Nd:YLF Laser," Journal of Refractive Surgery, 1996, vol. 12 (6), pp. 721-728.

(Continued)

*Primary Examiner* — Sam Yao
*Assistant Examiner* — Boniface N Nganga
(74) *Attorney, Agent, or Firm* — AMO Development LLC (57) ABSTRACT

An ophthalmic patient interface system includes an interface device and an ocular device. The interface device includes a frame having a first end and a second end, a lens disposed at the first end, and a skirt affixed to the first end. The second end is adapted to couple with a surgical laser system, and the skirt is adapted to seal against an anterior surface of an eye. The ocular device includes magnifying optics and is adapted to be removably seated within the second end. The magnifying optics image a region on a corneal side of the lens when the ocular device is seated within the second end.

2 Claims, 10 Drawing Sheets

(56) References Cited

U.S. PATENT DOCUMENTS

| | | |
|---|---|---|
| 5,141,506 A | 8/1992 | York |
| 5,171,254 A | 12/1992 | Sher |
| 5,174,254 A | 12/1992 | Humburg |
| 5,282,088 A | 1/1994 | Davidson |
| 5,336,215 A | 8/1994 | Hsueh et al. |
| 5,359,373 A | 10/1994 | Koester et al. |
| RE34,988 E | 7/1995 | Yang et al. |
| 5,548,352 A | 8/1996 | Dewey |
| 5,549,632 A | 8/1996 | Lai |
| 5,556,417 A | 9/1996 | Sher |
| 5,784,147 A | 7/1998 | Volk |
| 5,807,379 A | 9/1998 | L'esperance, Jr. |
| 5,984,915 A | 11/1999 | Loeb et al. |
| 5,984,916 A | 11/1999 | Lai |
| 5,997,559 A | 12/1999 | Ziemer |
| 6,140,630 A | 10/2000 | Rhodes |
| 6,247,473 B1 | 6/2001 | Yavitz |
| 6,254,595 B1 | 7/2001 | Juhasz et al. |
| 6,325,792 B1 | 12/2001 | Swinger et al. |
| 6,373,571 B1 | 4/2002 | Juhasz et al. |
| 6,436,113 B1 | 8/2002 | Burba et al. |
| 6,623,476 B2 | 9/2003 | Juhasz et al. |
| 6,638,305 B2 | 10/2003 | Laguette |
| 6,676,653 B2 | 1/2004 | Juhasz et al. |
| 6,863,667 B2 | 3/2005 | Webb et al. |
| 6,899,707 B2 | 5/2005 | Scholler et al. |
| 7,018,376 B2 | 3/2006 | Webb et al. |
| 7,611,507 B2 | 11/2009 | Raksi et al. |
| 2002/0103481 A1 | 8/2002 | Webb et al. |
| 2002/0167644 A1 | 11/2002 | Pollack et al. |
| 2005/0143718 A1 | 6/2005 | Rathjen |
| 2005/0192562 A1* | 9/2005 | Loesel et al. .................... 606/5 |
| 2005/0248724 A1 | 11/2005 | Jones |
| 2006/0192921 A1* | 8/2006 | Loesel et al. ................ 351/219 |
| 2007/0093795 A1* | 4/2007 | Melcher et al. ................ 606/10 |
| 2008/0103367 A1* | 5/2008 | Burba et al. ................ 600/236 |

FOREIGN PATENT DOCUMENTS

| | | |
|---|---|---|
| WO | WO9807053 A2 | 2/1998 |
| WO | WO0144871 A1 | 6/2001 |
| WO | WO2007050572 A2 | 5/2007 |

OTHER PUBLICATIONS

Juhasz T., et al., "Corneal Refractive Surgery with Femtosecond Lasers," IEEE Journal of Selected Topics in Quantum Electronics, 1999, vol. 5 (4), pp. 902-910.

* cited by examiner

OPHTHALMIC INTERFACE APPARATUS AND SYSTEM AND METHOD OF INTERFACING A SURGICAL LASER WITH AN EYE

CROSS-REFERENCE TO RELATED APPLICATIONS

This application is a divisional of U.S. patent application Ser. No. 11/948,433, filed Nov. 30, 2007, which is a continuation-in-part application of U.S. patent application Ser. No. 11/277,477, filed Mar. 24, 2006, which is a continuation application of U.S. patent application Ser. No. 10/865,165, filed Jun. 10, 2004, now U.S. Pat. No. 7,018,376, which is a divisional application of U.S. patent application Ser. No. 09/772,539, filed Jan. 29, 2001, now U.S. Pat. No. 6,863,667, the entire disclosure of each of these applications is incorporated herein by reference for all purposes.

FIELD OF THE INVENTION

The field of the present invention is generally related to patient interface systems and, more particularly, to ophthalmic interface apparatus and system and method for interfacing surgical lasers with an eye.

BACKGROUND

Many advances have been made in the area of ophthalmic surgery in recent years. In particular, lasers are being used more and more frequently in certain ophthalmic surgical procedures. For example, an ophthalmic surgical laser may be utilized to remove cataracts, re-shape the cornea, or the like. When providing therapy with the laser, one procedural aspect is to provide one or more reference points for aligning the laser. An accurate positioning of the eye in relationship to the laser allows the laser beam to be directed with a high degree of accuracy.

Devices have been constructed to stabilize the eye in relation to the laser. One example is a patient interface device. Patient interface devices typically have a corneal interface end and an attachment end for coupling to the laser. The corneal interface end is temporarily secured to a patient's cornea, and then the laser is docked to the attachment end to subsequently provide therapy. The corneal interface end typically uses a clear lens or interface glass to contact the cornea. This patient interface device is suited to stabilizing the eye and providing a fixed reference for accurate alignment of the laser with the patient's cornea. However, this and other patient interface devices lack mechanisms or tools that facilitate centering the interface device with respect to the patient's cornea. In some conventional patient interface devices, docking of the laser can be impeded by a limited field of view and/or the accumulation of moisture on the lens or interface contacting the cornea.

Accordingly, it is desirable to provide a system and method for interfacing a surgical laser with an eye and having a centering aid. It is also desirable to provide a system for interfacing a surgical laser with an eye that enhances viewing through the patient interface device. More particularly, it is desirable to provide a system for interfacing a surgical laser with an eye that assists in imaging, illuminating, or both imaging and illuminating a desired region of the eye. Additionally, it is desirable to provide a system for interfacing a surgical laser with an eye that increases the field of view and/or reduces moisture accumulation during patient interface. Additionally, other desirable features and characteristics of the present invention will become apparent from the subsequent detailed description and the appended claims, taken in conjunction with the accompanying drawings and the foregoing technical field and background.

SUMMARY OF THE INVENTION

Apparatus, systems, and methods are provided for interfacing a surgical laser with an eye. In one embodiment, a patient interface device is provided for supporting therapy provided by a surgical laser to an eye. The patient interface device includes a frame having a first end and a second end, a lens disposed at the first end, a skirt affixed to the first end, and an ocular device including magnifying optics. The second end of the frame is adapted to couple with the surgical laser. The lens has a corneal side. The skirt is adapted to seal against an anterior surface of the eye. The ocular device is adapted to be removably coupled with the second end, and the magnifying optics images a region on the corneal side of the lens when the ocular device is seated within the second end.

In another embodiment, a patient interface system is provided for supporting therapy provided by a surgical laser to an eye. The patient interface system includes an interface device and an ocular device. The interface device includes a frame having a first end and a second end, a corneal interface lens disposed at the first end, and a skirt affixed to the first end. The second end of the frame is adapted to couple with the surgical laser. The skirt is adapted to seal against an anterior surface of the eye. The ocular device includes magnifying optics and is adapted to be removably seated within the second end. The magnifying optics image a region on a posterior side of the corneal interface lens when the ocular device is seated within the second end.

In another embodiment, a patient interface system is provided for supporting therapy provided by a surgical laser to an eye. The patient interface system includes an interface device and a centration device. The interface device includes a frame having a first end and a second end, a corneal interface lens disposed at the first end, and a skirt affixed to the first end. The second end is adapted to couple with the surgical laser, and the skirt is adapted to seal against an anterior surface of an eye to form an annular chamber. The centration device includes a first portion adapted to be removably coupled within the second end, and a second portion contiguous with the first portion. The first portion includes an indicator identifying an optical axis of the interface device when the centration device is coupled to the interface device. The second portion is adapted to secure the first portion to the second end and release the first portion from the second end.

In another embodiment, a system is provided for interfacing a surgical laser, having an output surface, with an eye. The system includes a first piece having a first end and a second end, and a second piece having a first end and a second end. The first end of the first piece is adapted to couple to the surgical laser, and the second end of the first piece includes an interface lens contiguous with the output surface when the surgical laser is coupled to the first end of the first piece. The first end of the second piece is adapted to couple to the second end of the first piece, and the second end of the second piece is adapted to couple to the eye.

In yet another embodiment, a method of interfacing an ophthalmic surgical laser with an eye is provided. The method includes positioning an interface device above a cornea of the eye, the interface device comprising a frame having a corneal interface end and an attachment end, a corneal interface lens disposed at the corneal interface end of the frame, and a skirt affixed to the corneal interface end of the frame; setting the skirt against the eye such that a posterior surface of the corneal interface lens contacts an anterior surface of the cornea; coupling an ocular device within the attachment end of the frame, the ocular device comprising an indicator identifying an optical axis of the interface device and magnifying optics; aligning, via the ocular device, the optical axis of the interface device with a pupil within the eye; securing the skirt to the eye; decoupling the centration device from the attachment end of the frame; and engaging a surgical tip of the ophthalmic surgical laser with the attachment end of the frame. The posterior surface of the corneal interface lens and the anterior surface of the cornea each have a different curvature.

BRIEF DESCRIPTION OF THE DRAWINGS

One or more exemplary embodiments of the present invention will hereinafter be described in conjunction with the following drawings, wherein like reference numerals denote like components.

DETAILED DESCRIPTION

Apparatus, system, and method for interfacing an ophthalmic surgical laser system with an eye are provided having a centration aid. Generally, the centration aid assists in the alignment of an ophthalmic patient interface device (e.g., a disposable patient interface device or other patient interface device) with the cornea of an eye (e.g., for ophthalmic procedures utilizing the ophthalmic surgical laser system or to provide alignment of the ophthalmic patient interface device for other procedures). The centration aid is removably coupled with the patient interface device to facilitate alignment and the subsequent therapy utilizing the patient interface device. One example of a patient interface device is described in U.S. patent application Ser. No. 11/258,399, filed Oct. 24, 2005, the disclosure of which is incorporated herein by reference, although other patient interface devices may be utilized with one or more of the exemplary embodiments.

Figure 1:
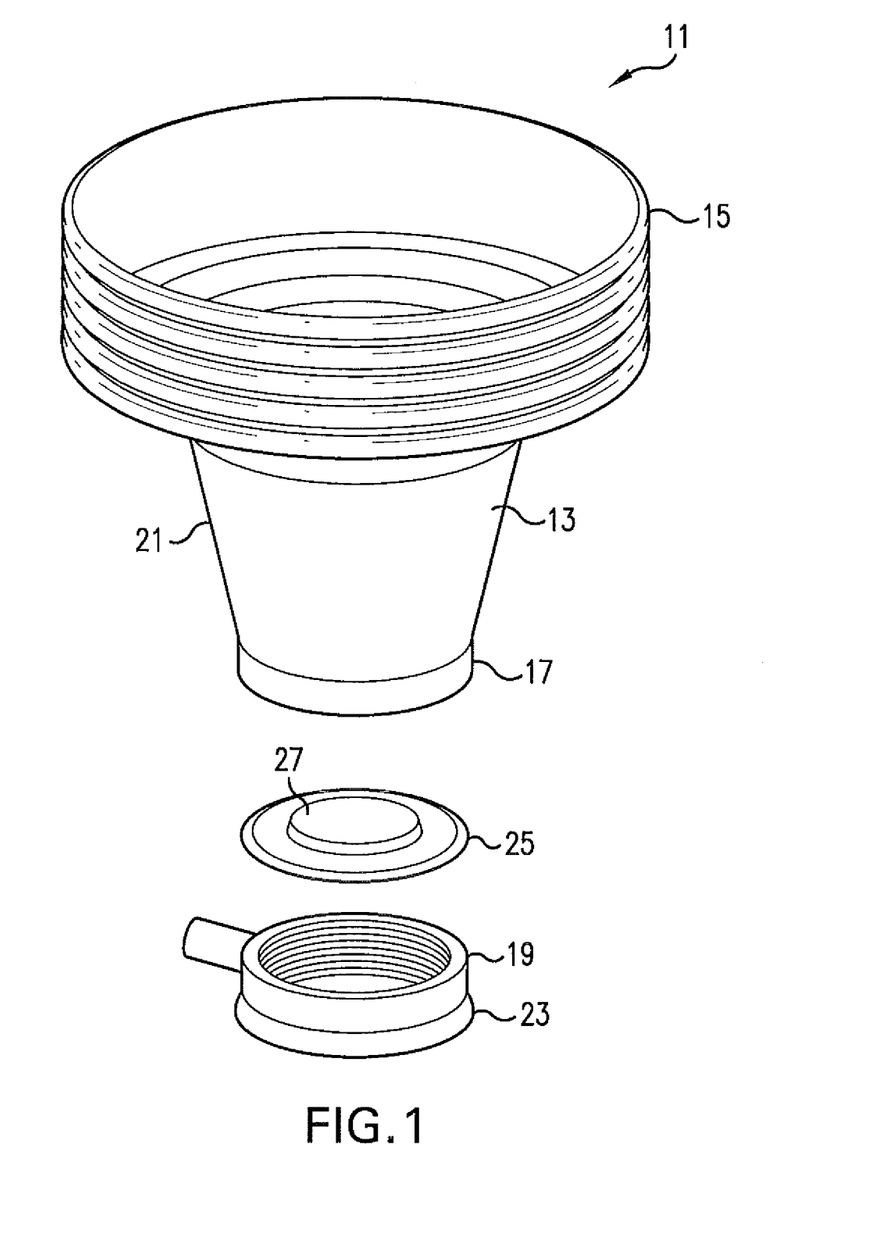
FIG. 1 is an exploded perspective view of a patient interface device in accordance with one embodiment.

Referring to the drawings, a patient interface device 11 is shown in FIG. 1 in accordance with one embodiment. In use, the patient interface device 11 is adapted to interface between an ophthalmic surgical laser system (not shown) and the cornea of an eye (not shown). The patient interface device 11 has a frame 13 with an attachment end 15 and a corneal interface end 17. In one embodiment, the frame 13 is generally conical shaped with the greater opening end forming the attachment end 15 and the constricted end forming the corneal interface end 17. The attachment end 15 of the frame 13 is preferably broad and open to accommodate an exit aperture of the ophthalmic surgical laser system. The corneal interface end 17 of the frame 13 is considerably narrower than the attachment end 15 to facilitate coupling with a retainer ring 19 and in turn, a patient's cornea. In this embodiment, the frame 13 also has non-perforated sidewalls 21. While the frame 13 is shown and described as having a conical shape, the shape is generally a matter of design choice. The lack of perforations in the sidewalls 21 reduces opportunities for cross-contamination between the eye and the ophthalmic surgical laser system during a surgical procedure. In another embodiment, the frame 13 may include perforations in the sidewalls 21, although such perforations should be located to maintain a sterile barrier between the eye and the ophthalmic surgical laser system. Although the frame 13 and retainer ring 19 are described as separate components, the frame 13 and retainer ring 19 may be constructed as a single, integrated piece.

The retainer ring 19 is constructed to be securely coupled with the corneal interface end 17. For example, the retainer ring 19 is constructed to have a snap fit with the corneal interface end 17 of the frame 13. A skirt 23 is affixed to the retainer ring 19 to enable the patient interface device 11 to engage a patient's cornea. Between the retainer ring 19 and the frame 13 is seated a flexible support 25, to which a corneal interface lens 27 is affixed in snap fit engagement. In one embodiment, the skirt 23 and the flexible support 25 are both annular, although other shapes may also be used. The skirt 23 may be flared, straight, or otherwise shaped to couple with the patient's cornea. The snap fitting between the retainer ring 19 and the frame 13 secures the flexible support 25. Although the retainer ring 19 is snap fit with the frame 13 to ease the separate manufacture of such components, other means for securing the retainer ring 19 with the frame 13 may be used.

Figure 2:
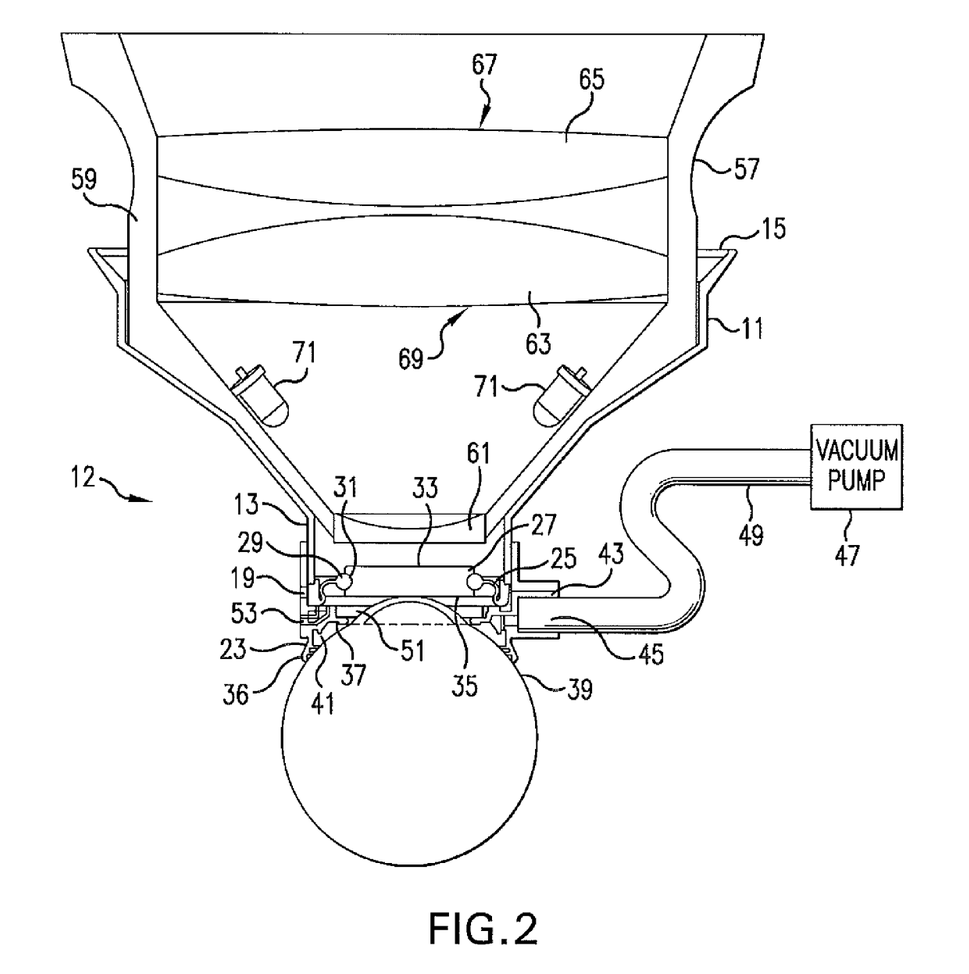
FIG. 2 is a sectional view of a patient interface system incorporating the patient interface device shown in FIG. 1 in accordance with one embodiment.

FIG. 2 is a sectional view of an ophthalmic patient interface system 12 incorporating the patient interface device 11 shown in FIG. 1 in accordance with one embodiment. In this embodiment, an ocular device 57 is shown coupled to (e.g., seated on) the attachment end 15 of the frame 13. The flexible support 25 is seated and secured between the retainer ring 19 and the frame 13. The inner annular surface of the flexible support 25 is formed with a bead 29 about a circumference of the inner annular surface, which engages a groove 31 formed in the side of the corneal interface lens 27. This arrangement enables the corneal interface lens 27 to snap fit into the flexible support 25. Adhesives or other methods known to the skilled artisan may also be used to affix the corneal interface lens 27 to the flexible support 25. In another embodiment, the flexible support 25 and corneal interface lens 27 are integrated together in a single unit. This embodiment may further facilitate disposability of one or more components of the patient interface device 11.

The corneal interface lens 27 has an anterior surface 33 and a posterior surface 35, and may be planar, as shown, or one or both of the surfaces 33, 35 may be curved. In operation, the posterior surface 35 of the corneal interface lens 27 contacts the cornea during the surgical procedure and flattens, configures, or otherwise shapes the cornea for the surgical procedure as the posterior surface 35 is applied to the cornea. In one embodiment, the corneal interface lens 27 has a geometrical configuration based upon the shape to which the cornea is to be conformed during the surgical procedure. The corneal interface lens 27 is preferably made of an inexpensive high strength transparent material, such as glass, plastic, or the like, although other transparent materials may be used.

The annular skirt 23 is preferably affixed to the retainer ring 19 using an adhesive which is appropriate for the materials used. Such an adhesive should be one that will not quickly deteriorate when exposed to light from lasers generally employed in ophthalmic surgical laser systems. The annular skirt 23 includes two flexible, annular walls 36, 37 extending away from the retainer ring 19. These annular walls 36, 37 form a channel which, when placed against the eye 39 as shown, form an annular chamber 41 in combination with the anterior surface of the eye 39. The skirt 23 also includes an arm 43 housing a passageway 45, which fluidly connects the annular chamber 41 with a vacuum pump 47 through a conduit 49 (e.g., a tube coupled to the arm 43). Examples of the vacuum pump 47 include a syringe or any other mechanical device capable of generating a negative pressure.

The patient interface device 11 is employed to substantially immobilize the eye during surgery. For this purpose, the skirt 23 is preferably constructed of a soft, pliable material. When the annular chamber 41 is formed by placing the skirt 23 against the eye 39, the vacuum pump 47 may be used to create negative pressure within the chamber, thereby coupling the skirt 23, and thus the patient interface device 11, to the eye 39.

During ophthalmic laser surgery, a secondary chamber 51 is typically created when the patient interface device 11 is coupled to the eye 39. In one embodiment, the secondary chamber 51 is formed by the posterior surface 35 of the corneal interface lens 27, the flexible support 25, the retainer ring 19, the annular skirt 23, and the cornea of the eye 39. The volume of the secondary chamber 51 varies based on the corneal interface lens 27 movement with respect to the flexible support 25 (e.g., the lens movement affects the extent to which the cornea is flattened, configured, or otherwise shaped for the surgical procedure. As the volume of the secondary chamber 51 varies, a localized variation of pressure typically occurs therein. This pressure variation can affect the desired cornea shaping (e.g., using the corneal interface lens 27).

Vent ports 53 are disposed within the retainer ring 19 and enhance controlled movement of the corneal interface lens 27. For example, the vent ports 53 equalize the relative pressure of air or fluids within the secondary chamber 51 with the pressure of the environment (e.g., atmospheric pressure). The vent ports 53 are preferably constructed so as not to compromise the sterile barrier between the eye 39 and the ophthalmic surgical laser system as well as the established pressure within the annular chamber 41. The retainer ring 19 may include a single vent port or multiple vent ports. With multiple vent ports, the ports are preferably regularly spaced in a ring about an axis (not shown) perpendicular to the corneal interface lens 27. The vent ports 53 help isolate the shaping of the cornea by the pressure applied to the posterior surface 35 of the corneal interface lens 27 (e.g., via the exit aperture of the ophthalmic surgical laser system). In one embodiment, the vent ports 53 are widened to substantially encircle the retainer ring 19. Free or forced air flow below the corneal interface lens 27 assists in preventing condensation of moisture and fogging on the corneal interface lens 27.

As part of the process of coupling the patient interface device 11 with the patient's eye 39, the corneal interface lens 27 is substantially centered with the pupil prior to reducing the pressure in the annular chamber 41. The ocular device 57 provides a centration aid and includes a sidewall 59 that is complimentary to the frame 13. For example, the sidewall 59 is constructed such that the ocular device 57 may be removably seated within the frame 13. The sidewall 59 internally supports magnifying optics, which are a series of lenses 61, 63, 65 in this embodiment. The magnifying optics are constructed and positioned to image and magnify a region near the posterior surface 35 of the lens 27 when the ocular device 57 is seated within the frame 13. Preferably, the magnifying optics provide a wide angle view of the region. Further, when the ocular device 57 is seated within the frame 13, the optical axis of the magnifying optics is substantially aligned with the optical axis of the corneal interface lens 27 and thus, the magnifying optics share an optical axis with the corneal interface lens 27.

Figure 3:
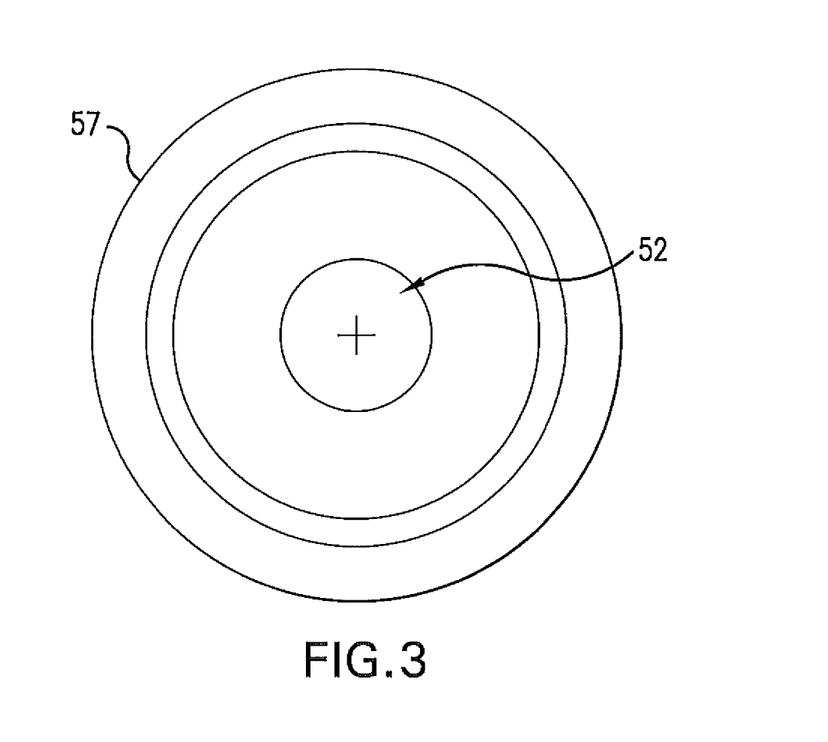
FIG. 3 is a top view of the ocular device shown in FIG. 2.

FIG. 3 is a top view of the ocular device 57 shown in FIG. 2 illustrating a centration indicator 52. In this embodiment, the magnifying optics of the ocular device 57 provide the centration indicator 52, which identifies the optical center of the magnifying optics. For example, referring to FIGS. 2 and 3, a first centration mark may be located on the anterior surface 67 of the first lens 65, and a second centration mark may be located on the posterior surface 69 of the second lens 63. Each of these centration marks identify the optical center of the magnifying optics. Multiple centration marks, such as when spaced-apart in relation to one another in this example, provide the advantage of reducing centration errors that may arise from parallax. In another embodiment, the ocular device 57 has a single centration mark. Other forms of centration indicators known to those skilled in the art may also be used. Thus, with the ocular device 57 coupled to the frame, the centration marks identify the optical axis of the corneal interface lens 27 as well as the patient interface device 11.

To illuminate the corneal interface lens 27, the ocular device 57 utilizes a light source that is coupled thereto. For example, LEDs 71 are included within the ocular device 57 and are positioned to illuminate the corneal interface lens 27.

During the process of coupling the patient interface device 11 with the patient's eye 39, the patient interface device 11 is positioned above the cornea and then the skirt 23 is set against the eye. As part of this process, the posterior surface 35 of the corneal interface lens 27 comes into contact with the cornea and at least part of the anterior surface of the cornea contours with the posterior surface 35 of the corneal interface lens 27, thus forming a visible contour boundary. This contour boundary is substantially circular in shape, and the position of the patient interface device 11 may be adjusted to center the contour boundary with the patient's pupil. While this centration may be done with the naked eye, the ocular device 57 facilitates the process by illuminating the contour boundary, and the cornea, by providing magnification of the region and by providing one or more centration marks or indicators. For example, the patient's pupil may be centered or aligned with the optical axis of the patient interface device 11 using the centration marks. Once the contour boundary is centered on the pupil, the skirt 23 is secured to the eye. For example, in one embodiment, the skirt 23 forms the annular chamber 41 in combination with the eye, and a negative pressure is generated in the annular chamber 41 to secure the position of the skirt 23 and thus the patient interface device 11. Other methods may also be used to secure the skirt 23 to the eye. The surgical tip of the ophthalmic surgical laser (e.g., associated with the exit aperture of the ophthalmic surgical laser system) is then engaged with the patient interface device 11, and the surgical procedure may proceed. Although not preferred, the patient interface device 11 may also be aligned with respect to other reference points of the eye using the centration indicator.

In one embodiment, the flexible support 25 and corneal interface lens 27 are positioned within the retainer ring 19 at a pre-determined distance, and this distance is selected for pre-applanation of the patient's cornea. For example, although not shown, by coupling the ocular device 57 to the patient interface device 11 (e.g., seating the ocular device 57 within the frame 13), the flexible support 25 displaces to a pre-determined extent to contact and pre-applanate the patient's cornea. The position of the flexible support 25 and corneal interface lens 27 within the retainer ring 19 and the extent of displacement for pre-applanation are preferably based at least on the dimensions of the ocular device 57, the position of the patient's cornea when the patient interface device 11 is coupled to the patient's eye 39, the flexibility of the flexible support 25, or any combination thereof. Additional factors may also be used to pre-determine the position of the flexible support 25 and the corresponding extent of displacement for pre-applanation. By pre-applanating the patient's cornea with the ocular device 57, another methodology is provided for centering the patient interface device 11 with respect to the patient's cornea. For example, the degree of pre-applanation can be selected to correspond with or mimic the degree of applanation desired during application of therapy by the ophthalmic surgical laser system.

Figure 4:
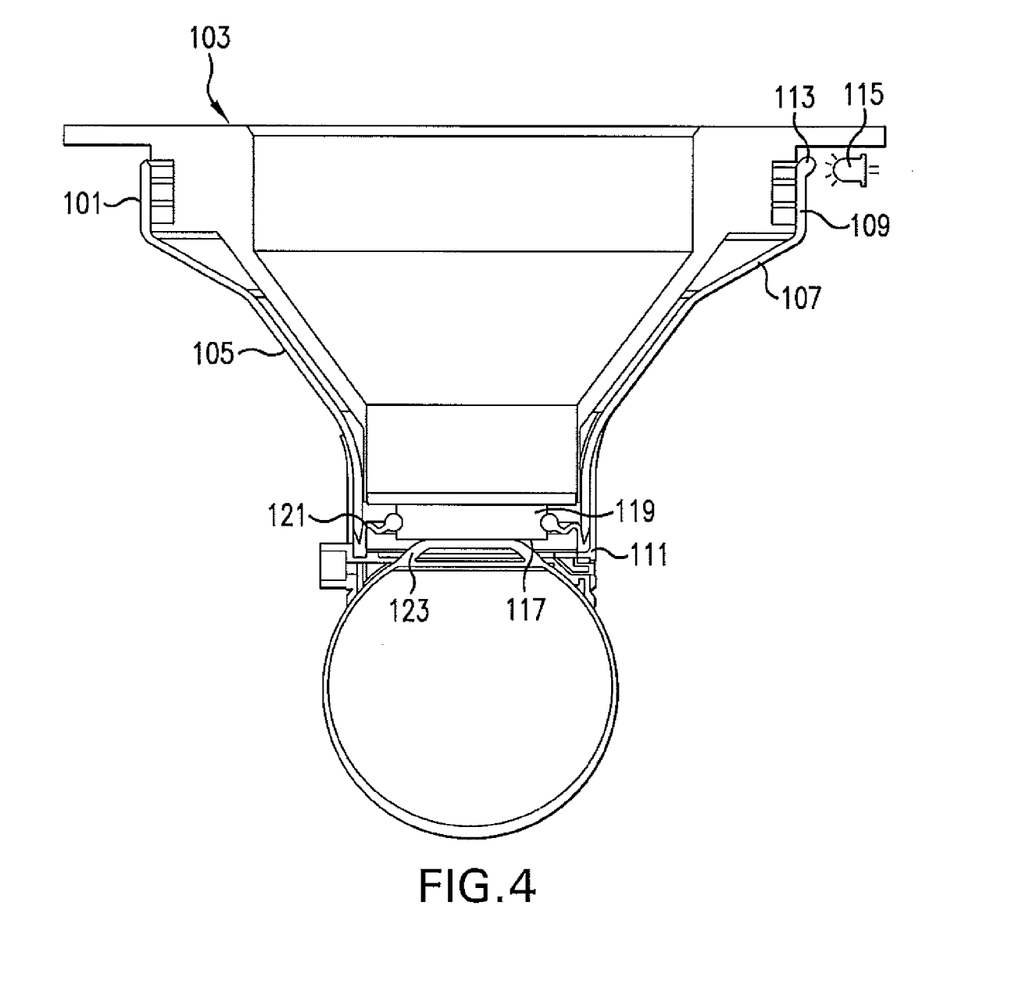
FIG. 4 is a patient interface device engaged with an ophthalmic surgical laser in accordance with another embodiment.

FIG. 4 is a sectional view of a patient interface device 101 engaged with a surgical tip 103 of the ophthalmic surgical laser in accordance with another embodiment. This patient interface device 101 has an engagement end 109, a corneal interface end 111, and a frame 105 that includes a light guide 107 extending from the engagement end 109 to the corneal interface end 111. At the engagement end 109, the light guide 107 includes a port 113 for receiving light from an external light source 115 (e.g., an LED) and direct light toward the corneal interface end 111. For example, the port 113 has a bulbous lip that receives and gathers light from the external light source 115. The corneal interface end 111 directs this gathered light out of the light guide 107 toward the region near a posterior surface 117 of the corneal interface lens 119.

The patient interface device 101 also includes a flexible support 121 that is formed of a material transparent to one or more spectra of visible light emitted by the light source 115, thus permitting light emerging from the light guide 107 to pass through the flexible support 121 and illuminate an indicated region of a cornea 123. In this embodiment, the light source 115 is separate from the patient interface device 101 to further facilitate ease of manufacturing and disposability of the device 101. Like the LEDs described above for the ocular device 57 (FIG. 2), the external light source 115 emits light in a visible spectrum and may be configured to emit light solely within a blue spectrum of visible light. Additionally, in one embodiment with vent ports (e.g., the vent ports shown in FIG. 2), the vent ports are preferably configured to prevent compromise of the sterile barrier between the eye and the surgical tip 103 of the laser or the ocular device 57 (FIG. 2).

Figure 5:
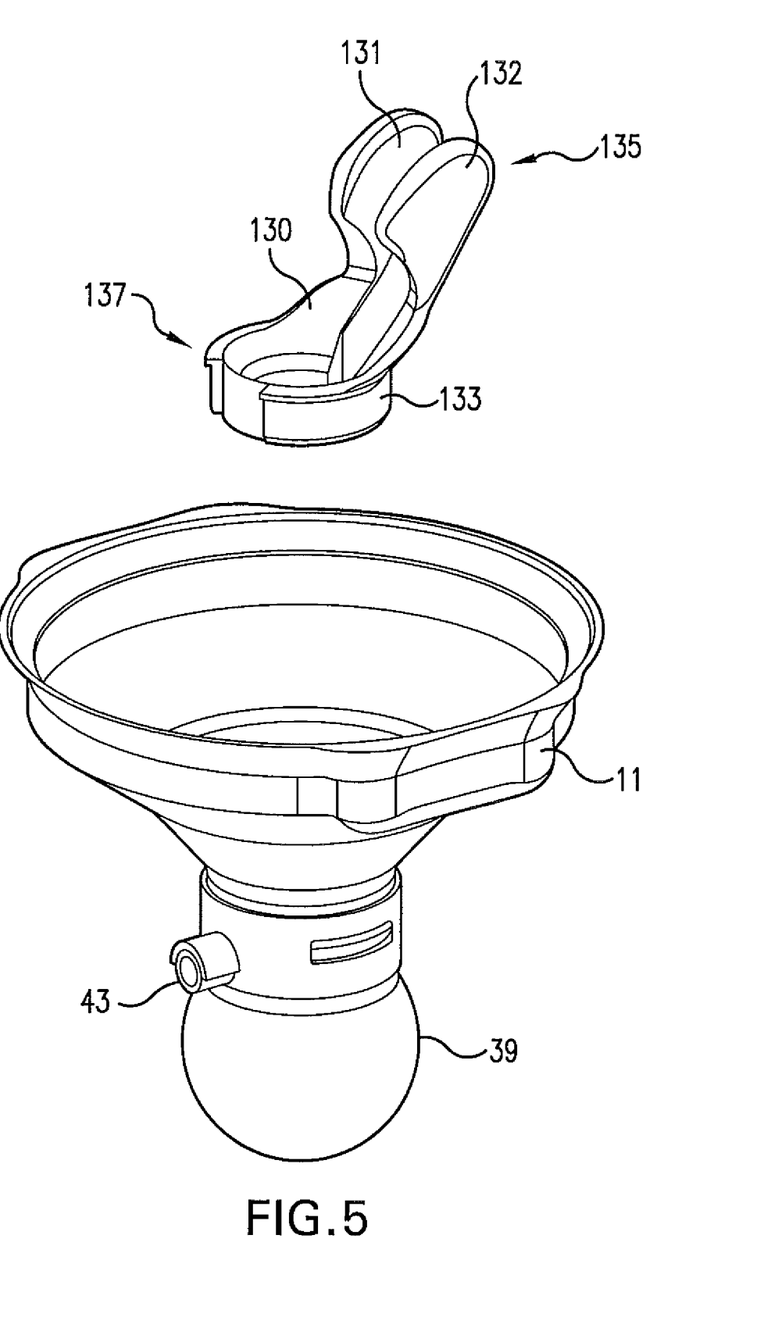
FIG. 5 is a perspective view of a centration device for use with the patient interface device shown in FIG. 2 in accordance with another embodiment.
Figure 6:
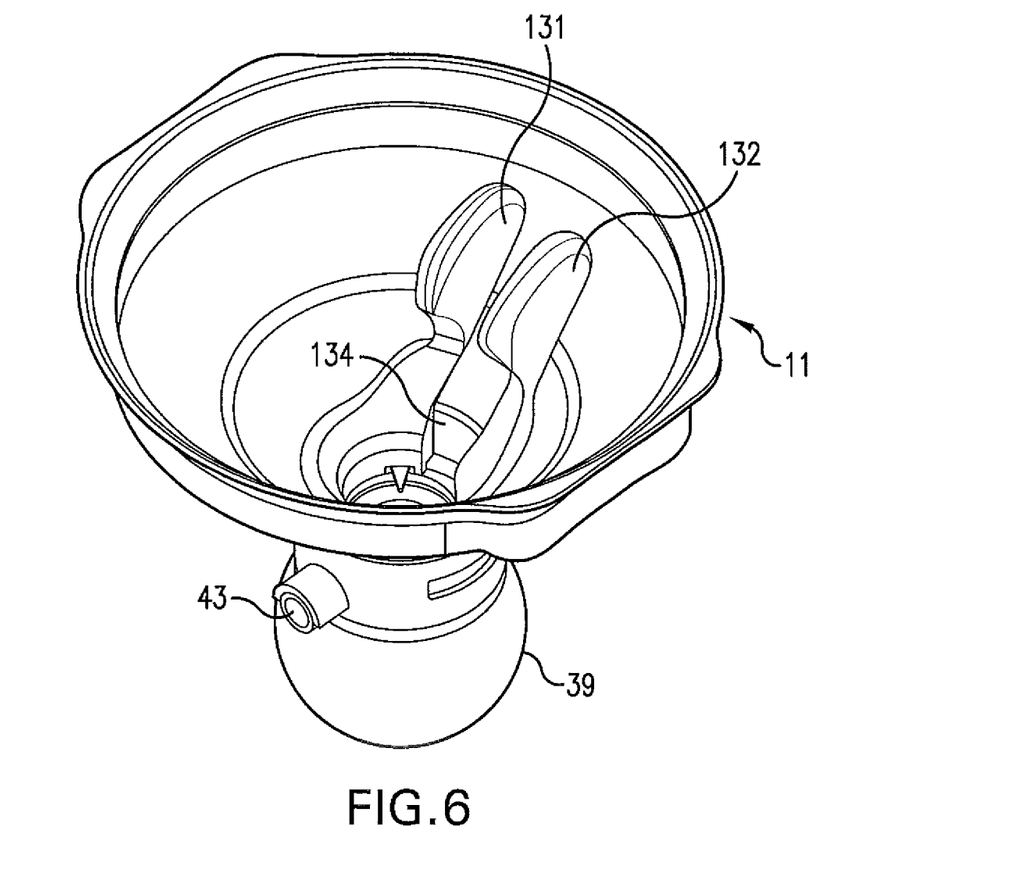
FIG. 6 is a perspective view of the patient interface device with the centration device shown in FIG. 5 coupled thereto.
Figure 7:
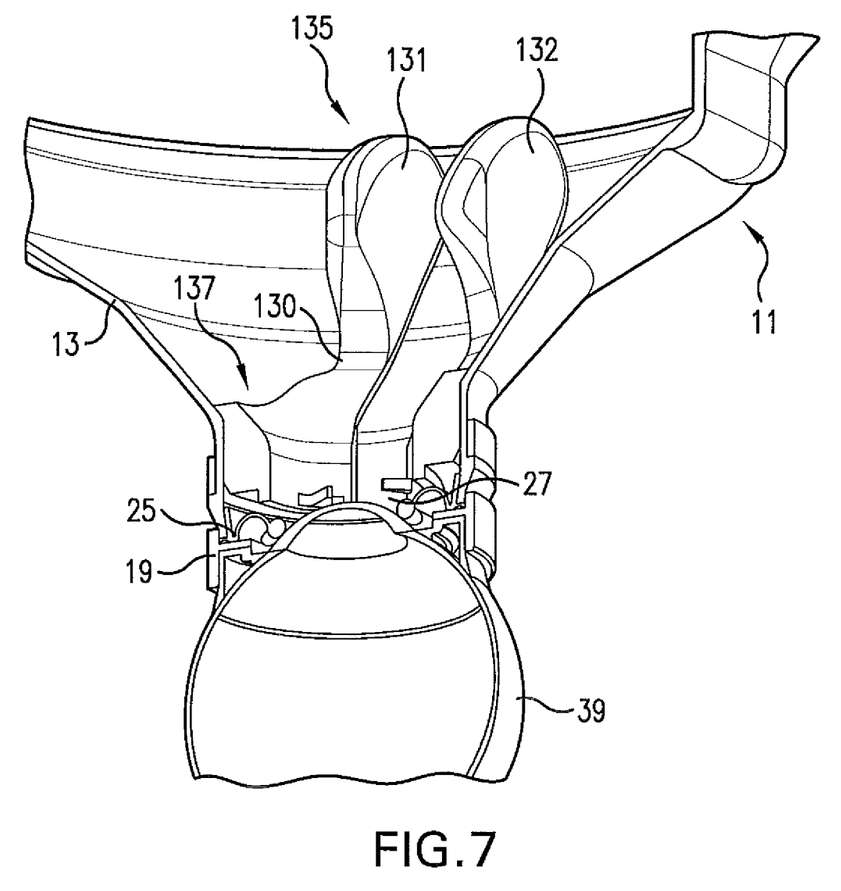
FIG. 7 is a sectional view of the patient interface device and the centration device shown in FIG. 6.
Figure 8:
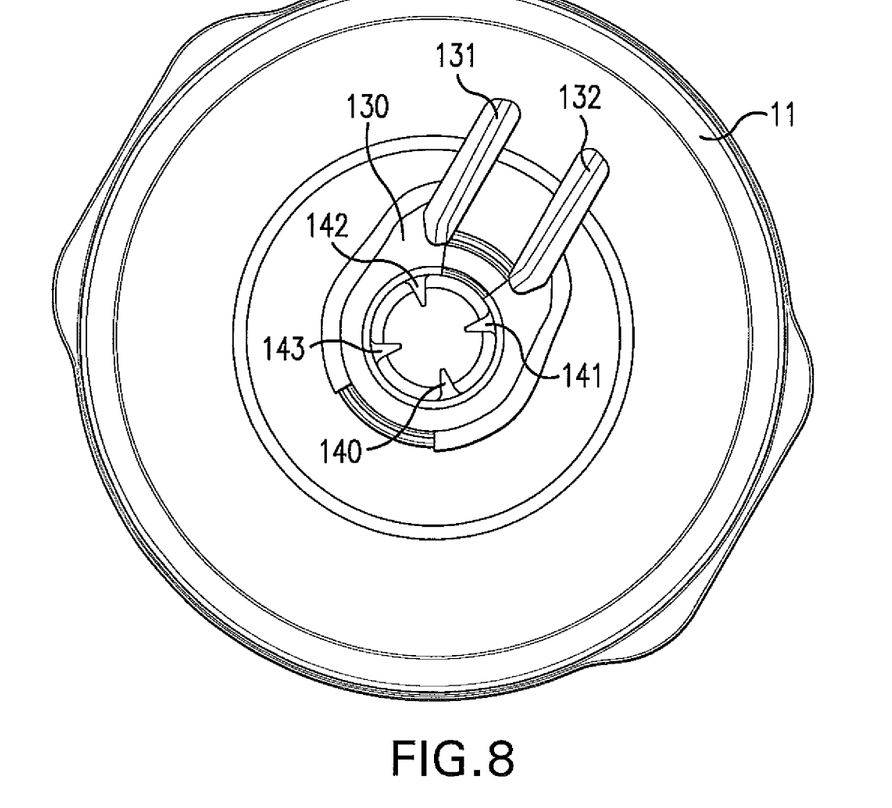
FIG. 8 is a top view of the patient interface device and centration device shown in FIGS. 6 and 7.

FIG. 5 is a perspective view of a centration device 130 for use with the patient interface device 11 shown in FIG. 2 in accordance with another embodiment, FIG. 6 is a perspective view of the patient interface device 11 with the centration device 130 shown in FIG. 5 coupled thereto, FIG. 7 is a sectional view of the patient interface device 11 with the centration device 130 shown in FIG. 6 coupled thereto, and FIG. 8 is a top view of the patient interface device 11 and centration device 130 shown in FIGS. 6 and 7. The centration device 130 may be removably coupled within the patient interface device 11 to provide yet another methodology for centering the patient interface device 11 with respect to the patient's cornea. In this embodiment, the centration device 130 has an attachment portion 137 for coupling to the frame 13 and has an interface portion 135 to assist in removing and coupling the centration device 130 to the patient interface device 11. The attachment portion 137 includes a centration indicator 140, 141, 142, 143, which identifies the optical center of the corneal interface lens 27 as well as the patient interface device 11. In this embodiment, the vent ports 53 shown in FIG. 2 are preferably configured to prevent compromise of the sterile barrier between the eye and the centration device 130.

The attachment portion 137 has an exterior surface 133 for coupling to an interior surface 134 of the frame 13. The interface portion 135 is angled from the attachment portion 137 (e.g., based on the shape of the frame 13) for ease of inserting and removing the centration device 130 with respect to the frame 13 while minimizing interference with centering the patient interface device 11 (e.g., maintaining a substantially unobstructed view of the centering aid). The interface portion 135 may be angled away from the optical center of the corneal interface lens 27 to a substantially similar degree as the corresponding portion of the frame 13.

In this embodiment, the interface portion 135 has first and second arms 131 and 132, respectively, that are coupled to the attachment portion for releasing and securing the attachment portion 137 with respect to the frame 13. For example, the centration device 130 may be fabricated from a semi-flexible or semi-rigid material, such as plastic, a plastic composite, or the like. When the attachment portion 137 is coupled to the frame 13, the exterior surface 133 is radially biased against the interior surface 134 of the frame 13 to secure the attachment portion 137 to the frame 13. By squeezing or pinching the bias arms 131 and 132 together, the shape of the exterior surface 113 is temporarily modified to decrease this bias and thereby release the attachment portion 137 from the frame 13. Other mechanisms (e.g., a bead-and-groove mechanism or the like) may also be used to secure and release the attachment portion 137 with respect to the frame 13. Additionally, the arms 131 and 132 are angled away from the optical axis of the patient interface device 11 and are preferably angled substantially parallel to the conical-shaped portion of the frame 13 substantially adjacent to the interface portion 135 when the centration device 130 is coupled to the patient interface device 11.

Similar to the pre-applanation when the ocular device 57 (FIG. 2) is coupled with the patient interface device 11, the flexible support 25 and corneal interface lens 27 may also be positioned within the retainer ring 19 at a pre-determined distance selected for pre-applanation of the patient's cornea utilizing the centration device 130. For example, by coupling the centration device 130 to the patient interface device 11 (e.g., securing the centration device 130 to the frame 13), the flexible support 25 displaces to a pre-determined extent to contact and pre-applanate the patient's cornea. The position of the flexible support 25 and corneal interface lens 27 within the retainer ring 19 and the extent of displacement for pre-applanation are preferably based at least on the dimensions of the attachment portion 137, the position of the patient's cornea when the patient interface device 11 is coupled to the patient's eye 39, the flexibility of the flexible support 25, or any combination thereof. Additional factors may also be used to pre-determine the position of the flexible support 25 and the corresponding extent of displacement for pre-applanation.

Figure 9:
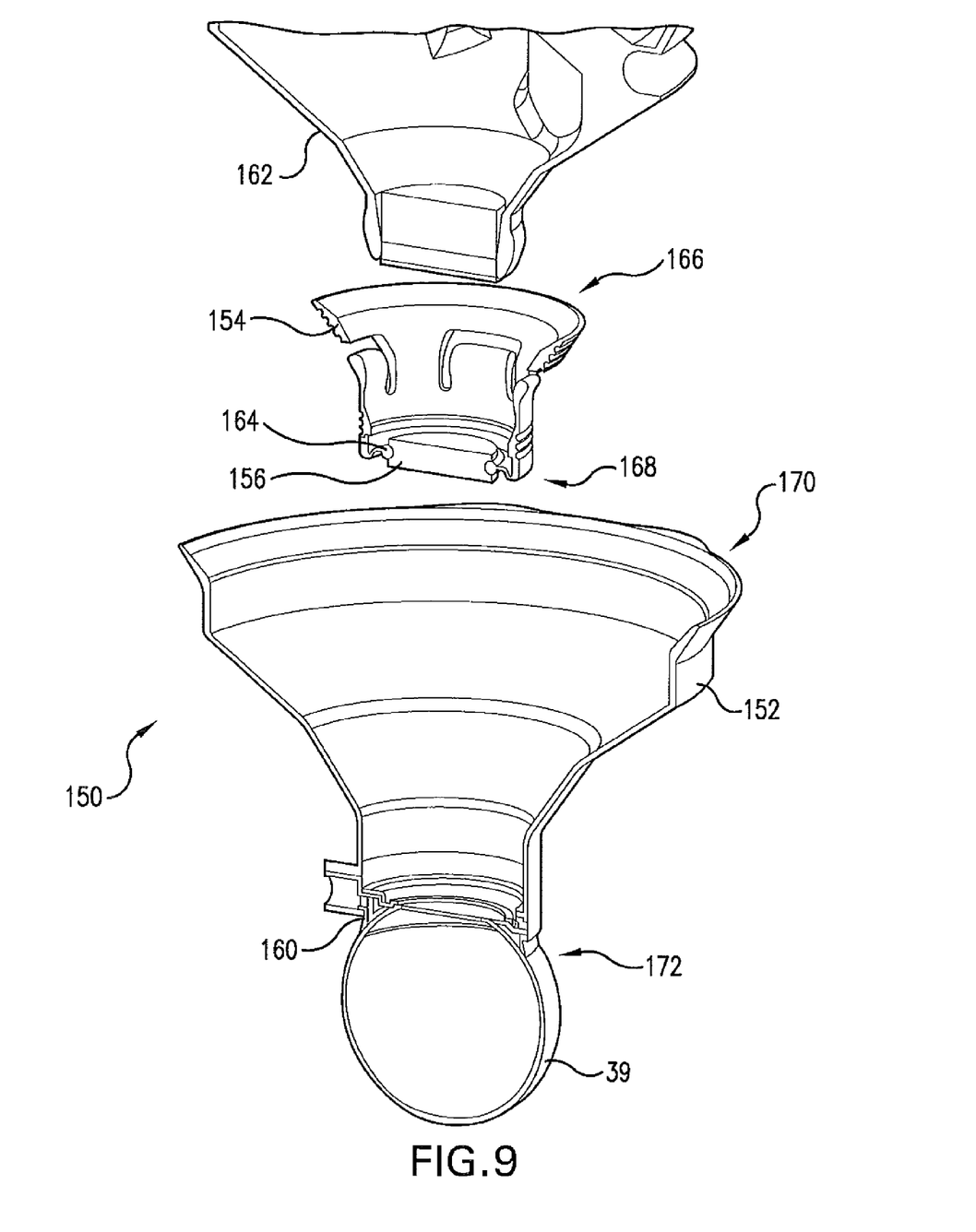
FIG. 9 is a sectional view of a patient interface device in accordance with another embodiment.
Figure 10:
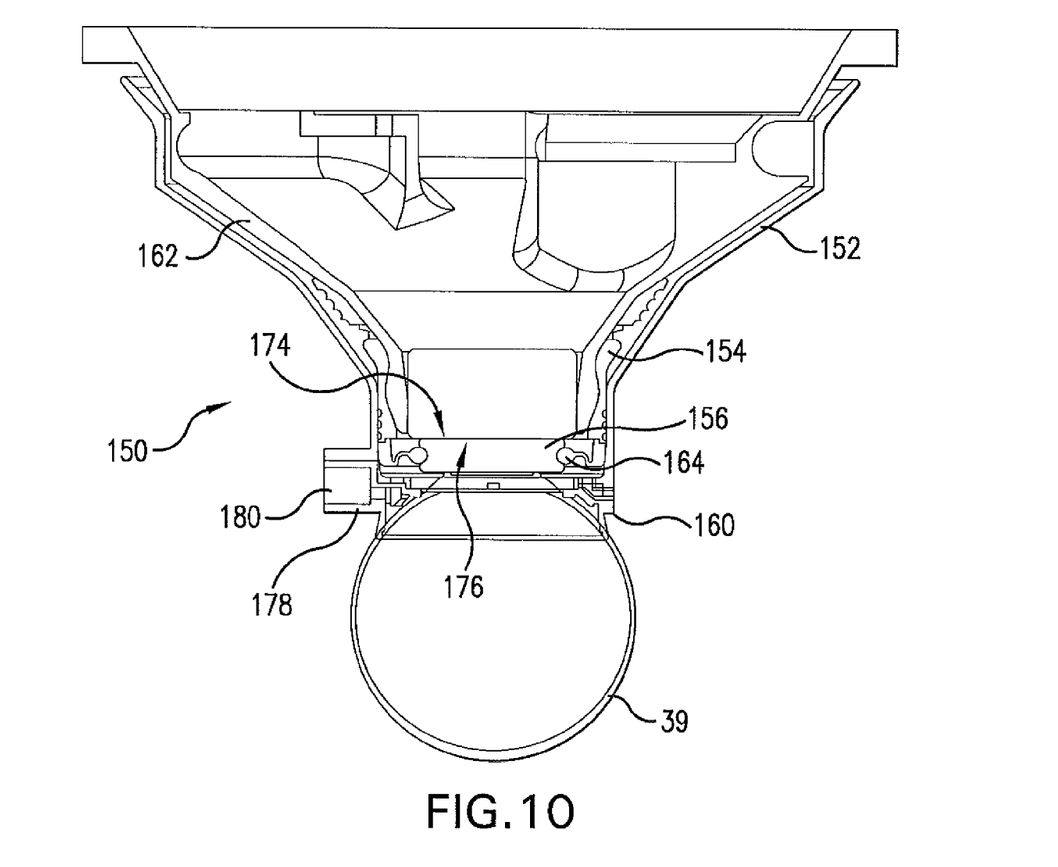
FIG. 10 is a sectional view of the patient interface device shown in FIG. 9 illustrating a laser head piece of the patient interface device docking with a corneal piece of the patient interface device.

FIG. 9 is a sectional view of a patient interface device 150 in accordance with another embodiment. FIG. 10 is a sectional view of the patient interface device 150 shown in FIG. 9 illustrating a laser head piece 154 of the patient interface device docking with a corneal piece 152 of the patient interface device. In this embodiment, the patient interface device 150 has two separate components, the laser head piece 154 and the corneal piece 152, which are not attached together or molded as a single unit, such as the patient interface device 11 shown in FIG. 2. The laser head piece 154 has a first end 166 for receiving and coupling to a laser head 162, such as may be used with an ophthalmic surgical laser system (not shown), and second end 168 with a corneal interface lens 156 for contacting the patient's eye 39. The corneal piece 152 has a first end 170 for receiving the laser head piece 154 and the laser head 162 (e.g., during docking) and a second end 172 for coupling to the patient's eye 39.

In one embodiment, the laser head piece 154 is a disposable piece having a temporary biasing portion (e.g., a snap-on ring) to snap-fit the laser head piece 154 onto the laser head 162. The laser head piece 154 is additionally rotation-resistant once fitted onto the laser head 162 to prevent twisting of the laser head piece 154 in relation to the laser head 162 and/or prevent abrasion of an output surface 174 of the laser head 162. With the laser head piece 154 coupled to the laser head 162, the output surface 174 is contiguous with an interior surface 176 of the corneal interface lens 156. The corneal interface lens 156 may be attached to the second end 168 of the laser head piece 174 via a flexible support 164 that is biased to abut the output surface 174 with the interior surface 176 with the laser head piece 154 coupled to the laser head 162.

The first end 170 of the corneal piece 152 is shaped to receive the laser head piece 154, and may also be shaped to receive a portion of the laser head 162 (e.g., when the first end 170 is cone shaped). The second end 172 of the corneal piece 152 includes a skirt 160 which, when placed against the eye 39 as shown, forms a chamber in combination with the anterior surface of the eye 39. The skirt 160 also includes an arm 178 that provides a conduit 180 in fluid connection with the chamber such that a negative pressure may be generated in the chamber (e.g., via a vacuum pump, a syringe, or any other mechanical device capable of generating the negative pressure).

In operation, the laser head piece 154 is coupled to the laser head 162, and the precision of this placement may be determined for any errors. The corneal piece 152 is coupled to the eye 39 by setting the skirt 160 onto the eye 39 and applying suction (e.g., generating a negative pressure within the chamber). Centration of the corneal piece 152 may be aligned using the ocular device 57 shown in FIG. 2 or centration device 130 shown in FIGS. 5-8 and removing/reapplying suction. The laser head piece 154 and laser head 162 are then coupled to the corneal piece 152 by guiding the second end 168 of the laser head piece 154 into the first end 170 of the corneal piece 152. The eye 30 may be applanated by contacting the corneal interface lens 156 with the cornea and applanating to a desired degree (e.g., by observing the size of a meniscus formed by the cornea in contact with the corneal interface lens 156). The corneal piece 152 may be locked to the laser head 162 after applanation and prior to directing laser beams to the eye 39. For example, the laser head 162 may have a bladder (not shown) around a portion adjacent to the first end 170 of the corneal piece 152. This bladder is inflated to bias the first end 170 of the corneal piece 152 against the laser head 162. Other mechanisms may be used to temporarily secure the laser head 162 against the corneal piece 152.

Using a two-piece configuration, the laser head piece 154, when coupled with the laser head 162, has a substantially unimpeded field of view (e.g., as viewed through the corneal interface lens 156). For example, the corneal interface lens 156 is coterminous with the second end of the corneal piece 152 without additional structure of the corneal piece 152 that may limit the field of view through the corneal interface lens 156. Additionally, the corneal interface lens 156 contacts the cornea after docking the laser head piece 154 and laser head 162 with the corneal piece 152, and thus the patient interface device 150 avoids accumulation of moisture (e.g., from the patient's eye 39) on the corneal interface lens 156 prior to actual contact with the cornea. The sufficiency of contact between the corneal interface lens 156 and the output surface 174 of the laser head 162 may be determined independent of and prior to docking the patient interface device 150 onto the patient's eye 39. Thus, placement errors that might be associated with coupling the corneal interface lens 156 with the laser head 162 may be corrected prior to the ophthalmic procedure.

Thus, a centration device, an ophthalmic patient interface device, an ophthalmic patient interface system, and a method of interfacing an ophthalmic surgical laser system with an eye are disclosed. While one or more embodiments have been shown and described, it will be apparent to those skilled in the art that more modifications are possible without departing from the inventive concepts herein. The invention, therefore, is not to be restricted except in the spirit of the following claims.

What is claimed is:

1. A patient interface system for supporting therapy provided by a surgical laser to an eye, the patient interface system comprising:
    an interface device comprising:
        a frame having a first end and a second end, wherein the second end is adapted to couple with the surgical laser;
        a corneal interface lens disposed at the first end, and
        a skirt affixed to the first end, wherein the skirt is adapted to seal against an anterior surface of the eye; and
    a centration device comprising:
        a first portion adapted to be removably coupled within the second end, the first portion comprising an indicator extending from a circumference of the first portion towards an optical axis of the centration device, the indicator identifying an optical axis of the corneal interface lens as well as the interface device when the centration device is coupled to the interface device; and
        a second portion contiguous with the first portion, the second portion adapted to secure the first portion to the second end and release the first portion from the second end;
    wherein the first portion is adapted to radially bias against an interior surface of the second end when the second portion secures the first portion to the second end,
    wherein the second end of the frame is angled away from the optical axis of the interface device, and
    wherein the second portion comprises first and second arms, the first and second arms both angled away from the optical axis of the interface device and substantially parallel with the second end of the frame.

2. The system of claim 1, wherein the interface device further comprises a flexible support affixing the corneal interface lens to the frame, and wherein the flexible support is adapted to displace a pre-determined distance towards the eye when the centration device is seated within the second end, the pre-determined distance based on a pre-applanation of the eye by the corneal interface lens.

* * * * *